United States Patent [19]

Taylor

[11] Patent Number: 4,950,265
[45] Date of Patent: Aug. 21, 1990

[54] ARMING DEVICE FOR A MEDICAL INSTRUMENT

[75] Inventor: Glenn N. Taylor, Longmont, Colo.

[73] Assignee: Hart Enterprises, Inc., Wyoming, Mich.

[21] Appl. No.: 258,510

[22] Filed: Oct. 17, 1988

[51] Int. Cl.$^5$ ............................................. A61B 17/00
[52] U.S. Cl. ...................................... 606/1; 128/749; 604/134
[58] Field of Search .................. 128/749, 751-755, 128/303 A, 303 R, 321; 604/134-139, 151, 157; 606/205-209

[56] References Cited

U.S. PATENT DOCUMENTS

| | | | |
|---|---|---|---|
| 2,556,783 | 5/1950 | Wallace | 128/321 |
| 4,393,872 | 7/1983 | Reznik | 604/151 |
| 4,602,631 | 7/1986 | Funatsu | 128/321 |

FOREIGN PATENT DOCUMENTS 2194748 3/1988 United Kingdom ................ 128/321

Primary Examiner—Max Hindenburg
Assistant Examiner—Kevin Pontius
Attorney, Agent, or Firm—Thomas R. Vigil; James P. Hanrath

[57] ABSTRACT

The arming device for use in manipulating with one hand a medical instrument comprises first and second telescoping members. The instrument members are longitudinally movable relative to one another, and the device comprises an arcuate flexible member having a forward portion and a rearward portion with means at the forward portion for engaging the first member of the instrument and means at the rearward portion for engaging the second member whereby squeezing of the flexible member laterally toward the instrument causes the first and second telescoping members to move longitudinally away from each other thereby to cause arming or operation of the instrument. The method of using the arming device comprises the steps of connecting a distal end of a distal longitudinally movable telescoping member of a medical instrument to first engaging means of the device and connecting a proximal end of a proximal longitudinally movable telescoping member of the medical instrument to second engaging means of the device which is spaced from the first engaging means; placing an assembly of the device with the instrument members engaged thereto in the palm of the hand; and placing a squeezing force, directed laterally toward the instrument, upon at least an area of the device which lies alongside the medical instrument between the engaging means to flex the device, elongating the device along an axis parallel to a central longitudinal axis of the instrument to cause the telescoping members of the instrument to move longitudinally away from one another.

21 Claims, 3 Drawing Sheets

ARMING DEVICE FOR A MEDICAL INSTRUMENT

BACKGROUND OF THE INVENTION

1. Field of the Invention

The present invention relates to an arming device for use with a medical instrument, such as a biopsy instrument, which allows the instrument to be armed, or readied for use, with one hand.

2. Description of the Prior Art

Heretofore an instrument for performing a biopsy, such as a core biopsy, has been proposed in applicant's copending U.S. patent application Ser. No. 150,984 for: SOFT TISSUE CORE BIOPSY INSTRUMENT, the teachings of which are incorporated herein by reference. The instrument is operable with one hand.

The arming device of the present invention is designed for use with the core biopsy instrument referred to above or for use with a syringe-type instrument for performing an aspiration biopsy. The arming device is squeezed to extend longitudinally movable sections of the instrument away from each other to arm or operate the instrument.

SUMMARY OF THE INVENTION

According to the invention there is provided an arming device for use in manipulating with one hand a medical instrument comprising first and second telescoping members, said instrument members being longitudinally movable relative to one another, said device comprising a medical instrument having first and second telescoping members longitudinally moveable relative to one another;

an arcuate flexible member having a forward portion and a rearward portion;

first means at said forward portion for engaging said first telescoping member and second means at said rearward portion for engaging said second telescoping member whereby squeezing of said flexible member laterally toward said instrument causes said first and second telescoping members to move longitudinally away from each other thereby to cause arming or operation of the instrument.

Further according to the invention there is provided a method of using an arming device comprising the steps of:

connecting a distal end of a distal longitudinally movable telescoping member of a medical instrument to first engaging means of the device;

connecting a proximal end of a proximal longitudinally movable telescoping member of the medical instrument to second engaging means of the device, said second engaging means being spaced from said first engaging means;

placing an assembly of the device with the instrument members engaged thereto in the palm of the hand; and placing a squeezing force, directed laterally toward the instrument, upon at least an area of the device which lies alongside the medical instrument between the engaging means to flex the device, elongating the device along an axis parallel to a central longitudinal axis of the instrument to cause the telescoping members of the instrument to move longitudinally away from one another.

DESCRIPTION OF THE PREFERRED EMBODIMENT

Figure 1:
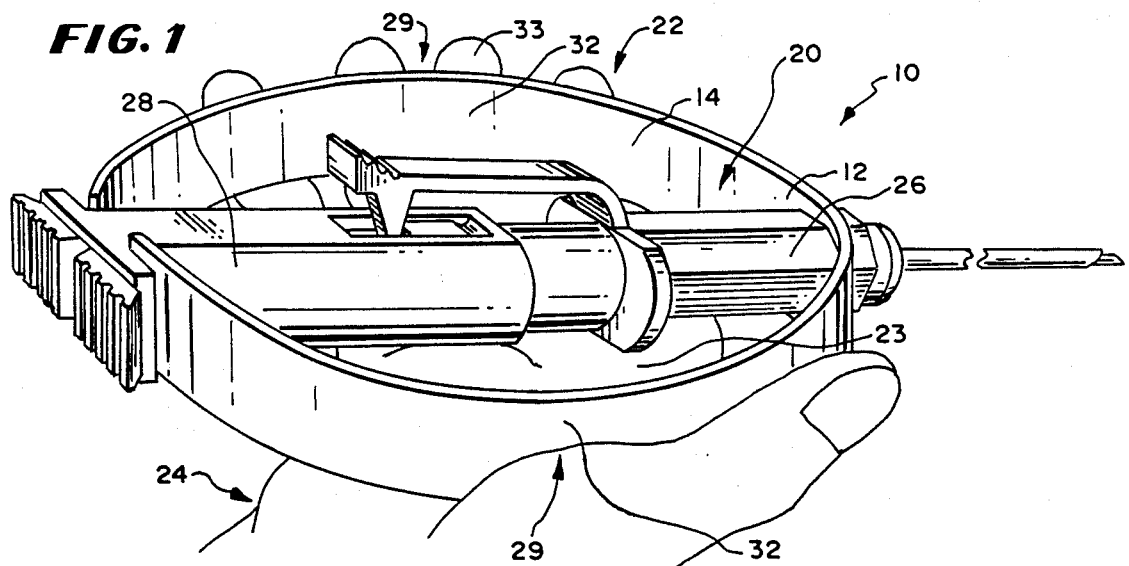
FIG. 1 is a perspective view of one embodiment of a circular arming device of the present invention attached to a biopsy instrument, with the arming device and instrument positioned in the hand of a user.

Referring now to the drawings in greater detail, there is shown in FIG. 1 a first embodiment of an arming device 10 constructed in accordance with the teachings of the present invention. The arming device 10 comprises an arcuate flexible member 12 which in this embodiment includes a circular ring 14 which is made of a flexible or deformable material, such as stainless steel, polycarbonate, polypropylene or ABS.

The ring 14 is shown attached to or mounted onto a biopsy instrument 20. The biopsy instrument 20 can be of the type disclosed in copending U.S. patent application Ser. No. 150,984 or: SOFT TISSUE CORE BIOPSY INSTRUMENT, the disclosure of which is incorporated herein by reference.

The arming device 10 with attached biopsy instrument 20 forms an assembly 22 which is shown resting in the palm 23 of a user's hand 24, substantially as the user would hold the assembly 22 for use.

The biopsy instrument 20 comprises two telescoping barrel members 26 and 28 which are longitudinally movable relative to one another. The instrument 20 is shown being "armed" or readied for use by the placement of a compressive force, at 29, upon areas 32 of the ring 14, lying generally parallel to a longitudinal axis of, and alongside of, the instrument 20, by fingers 33 of the user's hand 24.

Figure 2:
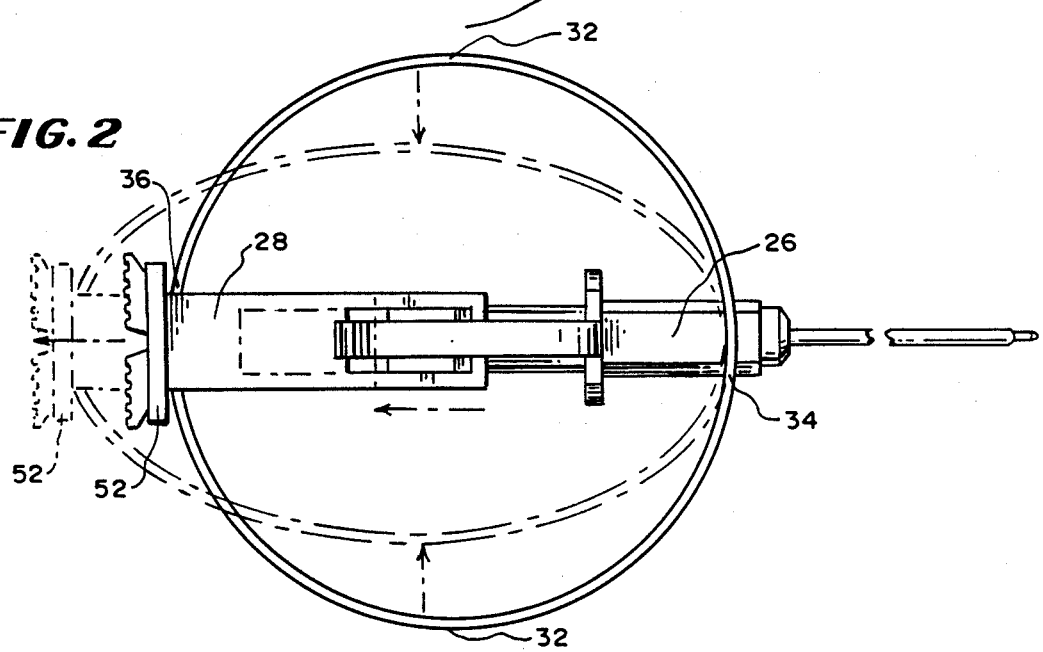
FIG. 2 is a top plan view of a biopsy instrument with the arming device of the present invention attached thereto and shows, in phantom, the distorting of the arming device and longitudinal separation of telescoping members of the instrument.

As better illustrated in FIG. 2, when a compressive force is applied to the areas 32 of the ring 14, the ring 14 is deformed to an oval shape, as shown in phantom. Since each of the barrel members 26, 28 is attached to the ring at forward and rearward points 34, 36, respectively, with the points 34, 36 being directly opposite one another along a diameter of the ring 14, this deformation produces a separation of the barrel members 26 and 28 in the longitudinal direction, which "arms" or readies the instrument 20 for use as described in copending application Ser. No. 150,989.

Figure 3:
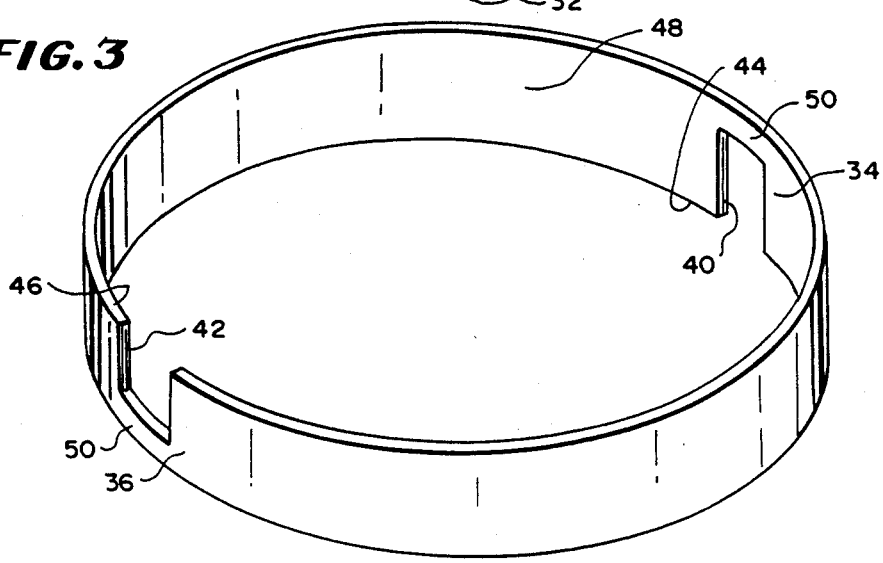
FIG. 3 is a perspective view of the arming device of FIG. 1, detached from the biopsy instrument.

As shown in FIG. 3, the ring 14 is provided with two openings or notches 40 and 42 at the opposed points 34, 36, on the ring 14. The notches 40 and 42 are shown to be rectangular, each notch 40, 42 extending from an opposite side edge 44 or 46 of the ring 14 into a wall 48 of the ring 14.

The notch 40 is sized and configured to receive the barrel member 26 therein. For the purpose of engaging the barrel member 26 within the notch 40, a peripheral, partially or fully annular groove (not shown) may be provided in the barrel member 26, within which a wall area 50 of the ring 14 surrounding and at the edge of the notch 40 may be received.

The notch 42 is sized and configured to fit over the barrel member 28, just forward of a rear flange 52 (FIG. 2) of the barrel member 28. When the ring 14 is deformed or squeezed against the instrument 20, the wall area 50 of the ring 14 surrounding the notch 42 pushes against this flange 52 while the wall area 50 surrounding the notch 40 pushes against a distal wall of the groove (not shown) in the barrel member 26 to cause the two barrel members 26 and 28 to separate longitudinally.

During the process of separating the two barrel members 26 and 28, the instrument 20 is "armed" for use, as disclosed in copending U.S. patent application Ser. No. 150,984, referred to above.

Use of the arming device 10, however, need not be limited to use with the core biopsy instrument 20.

Figure 4:
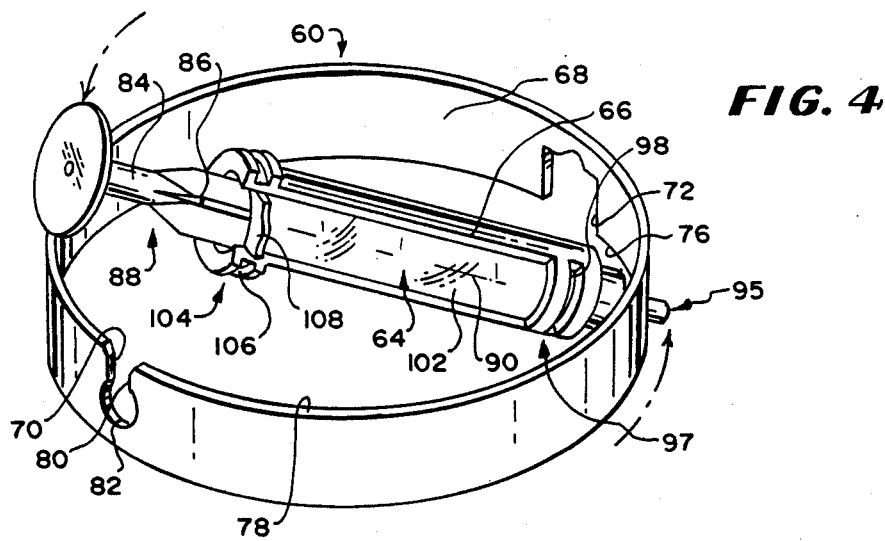
FIG. 4 is a perspective view of a second embodiment of a circular arming device of the present invention and a syringe being placed within the device and showing a syringe housing having peripheral slots or grooves therein for receiving edges of the arming device.
Figure 5:
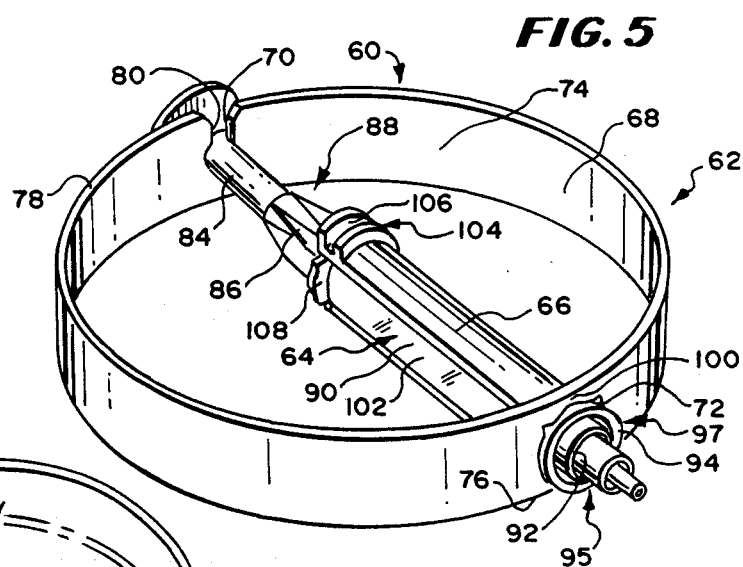
FIG. 5 shows the syringe attached to the circular arming device.

In FIGS. 4 and 5, a syringe arming device 60 is illustrated and forms a second embodiment of the arming device of the present invention. The arming device 60 forms part of an assembly 62 including a syringe 64 for one handed operation and control of the syringe 64, such as during an aspiration biopsy.

In this embodiment, the syringe arming device 60 can include a syringe mounting sleeve 66 in addition to a ring 68 which is made of a deformable material and is similar to the ring 14 shown in FIGS. 1–3. Two openings or notches 70 and 72 again are provided at first (forward) and second (rearward) points on the ring 68 and extend into a wall 74 of the ring 68 from opposite side edges 76 and 78 thereof, respectively.

The notch 70 has a neck portion 80 which connects with a larger rounded portion 82, and is sized and configured to receive a proximal end portion 84 of a shaft 86 of a plunger 88 of the syringe 64 therein in a snap fit manner.

The sleeve 66 is received about a barrel 90 of the syringe 64. The sleeve 66, as shown in FIGS. 4 and 5, is sized and configured to engage securely about the syringe barrel 90 and has an opening 92 in a forward end 94 thereof, through which a needle hub 95 of the barrel 90 can extend.

Proximal to the forward end 94, the sleeve 66 has a circumferential groove 98 therein as shown in FIG. 4, which receives a wall portion 100 of ring 68 surrounding the notch 72 therein.

To facilitate engagement of the sleeve 66 onto the syringe barrel 90, the sleeve 66 has a longitudinal channel 102 therein. The sleeve 66 also has at least one circumferential boss 104 at a proximal end thereof with a circumferential groove 106 therein. Although not shown in FIG. 4, an elongate slot is provided within the sleeve 66 and boss 104 and communicates with the groove 106 directly opposite the longitudinal channel 102 for receiving one of two finger flanges 108 (the one hidden from view) on the syringe barrel 90 therein for locking the syringe barrel 90 within the sleeve 66 against longitudinal movement.

In use of the arming device 60, the sleeve 66 is slipped over the syringe barrel 90, the plunger 88 is snapped into engagement in the notch 72 provided therefor and the groove 98 receives the wall area at the edge of the notch 70, completing the assembly 62, as shown in FIG. 5.

Figure 6:
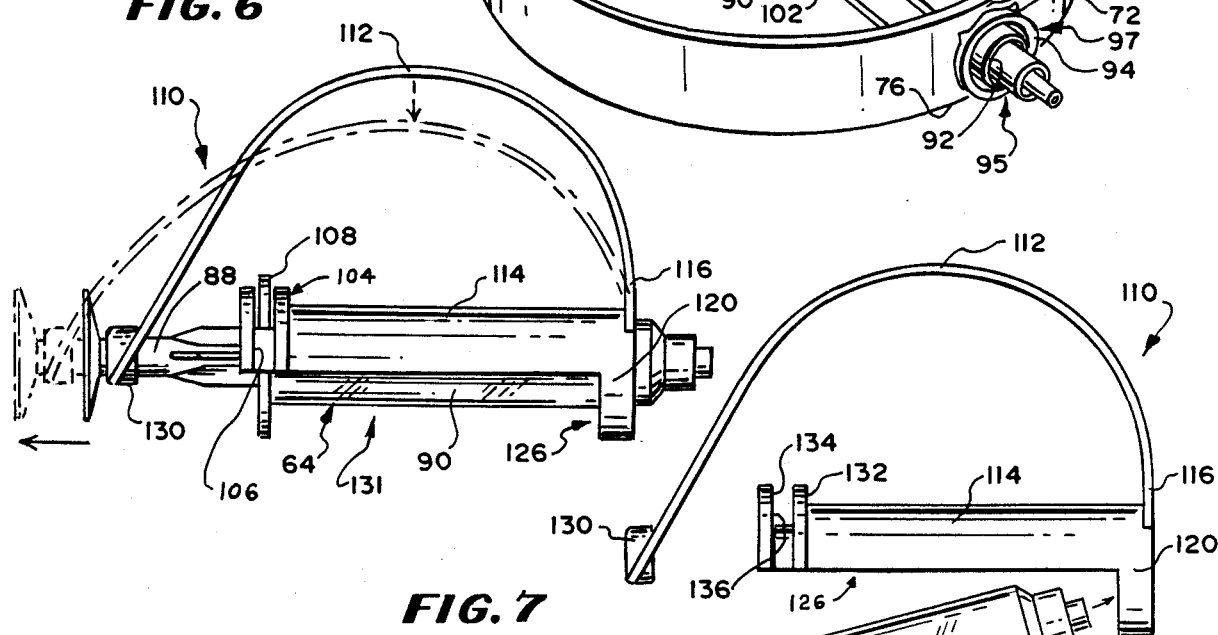
FIG. 6 is a plan view of a third embodiment of a semi pear or semi teardrop shaped arming device including a syringe holding sleeve received over a syringe barrel and shows, in phantom, deformation of the arming device to extend a plunger of the syringe proximally out of the syringe barrel.
Figure 7:
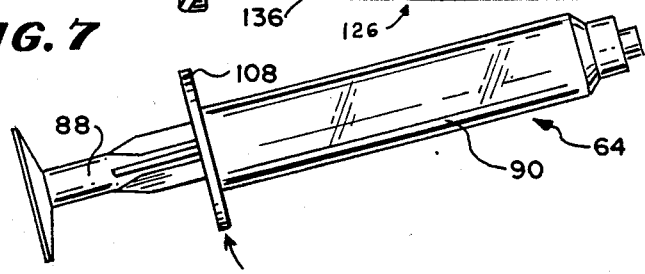
FIG. 7 is a plan view of the device shown in FIG. 6 and shows the syringe being inserted into the syringe holding sleeve of the device.
Figure 8:
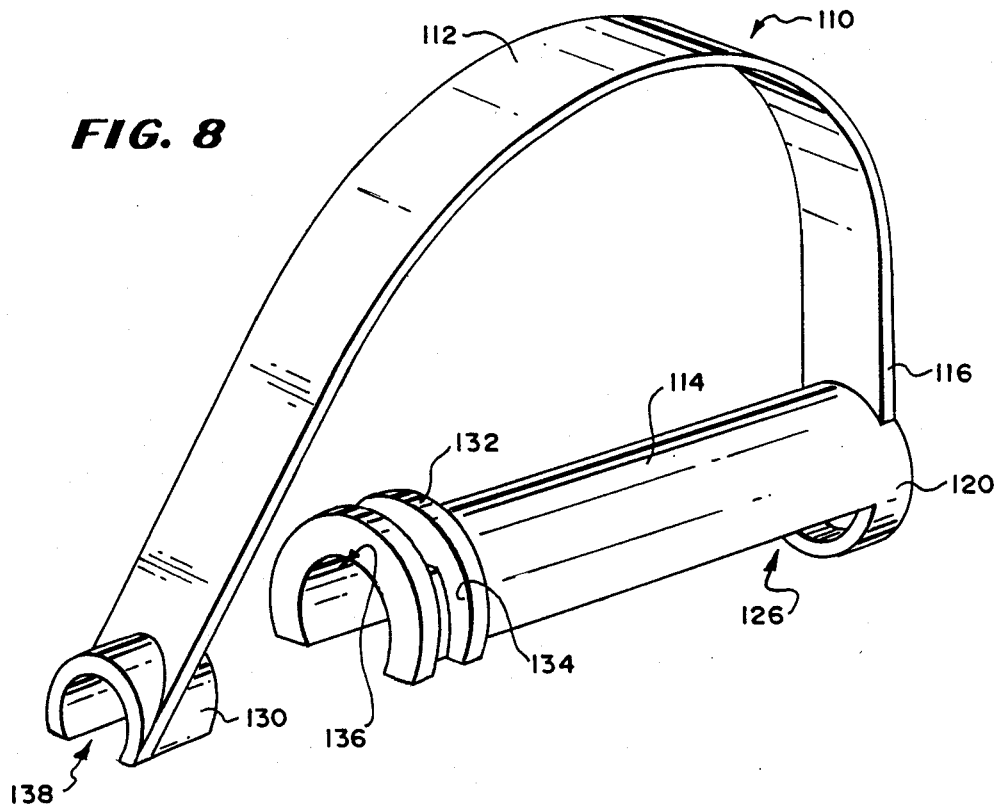
FIG. 8 is a rear perspective view of the device shown in FIGS. 6 and 7.

Another embodiment of a syringe arming device 110 which is an arcuate flexible hemicircular or hemi teardrop shaped (or hemi pear shaped) member 112 is shown in FIGS. 6–8. The arming device 110 includes a sleeve 114 which receives the syringe barrel 90 therein and which is integral with a forward end 116 of the member 112.

The member 112 extends arcuately from its forward end 116 fixed to a forward end 120 of the sleeve 114. As shown, a portion of the sleeve 114 is cut away to form a longitudinal channel 126 which extends toward the forward end 120. The member 112 extends from the forward end 116 rearwardly to a proximal semi-annular collar 130 which snap fits over the plunger 88 of the syringe 64. Use of the hemi circular or hemi tear drop shape of the member 112 in place of a ring provides for a more compact assembly 131.

In using the device 110, the syringe barrel 90 with the sleeve 114 therearound will be placed against a heel of the user's palm 23 and the user's fingers 30 will compress or squeeze the arcuate member 112 against the sleeve 114 to deform the member 112, thereby extending the plunger 88 outwardly from the syringe barrel 90, and maintaining such extension during removal of the syringe 64 from the point of aspiration biopsy.

As illustrated in FIG. 7, in forming the assembly 131 the syringe barrel 90 first will be inserted into the sleeve 114 in a manner similar to that described in connection with FIG. 5. In this respect, the sleeve 114 is provided with a circumferential boss 132 at a proximal end thereof with a groove 134 therein. An elongate slot 136 is provided in the boss 132 and communicates with the groove 134 opposite the channel 126 through which one finger flange 108 of the syringe barrel 90 extends, locking the barrel 90 against longitudinal movement within the sleeve 114. Next, the plunger 88 of the syringe 64 is engaged in a snap fit within the proximal collar 130 of the arm 116.

As shown in FIG. 8, which is a rear perspective view of the device 110, the proximal collar 130 has a channel 138 therein, through which the plunger 88 of the syringe 64 is pressed until it snaps into the collar 130. Also, the sleeve 114 is shown here to be of a cylindrical configuration, and again shows the provision of the slot 136 within a boss 132 thereof for receiving one finger flange 108 of the syringe barrel 90 therein. It will be understood that the syringe arming device 110 is unitary and, again, is made of any suitable flexible material.

Figure 9:
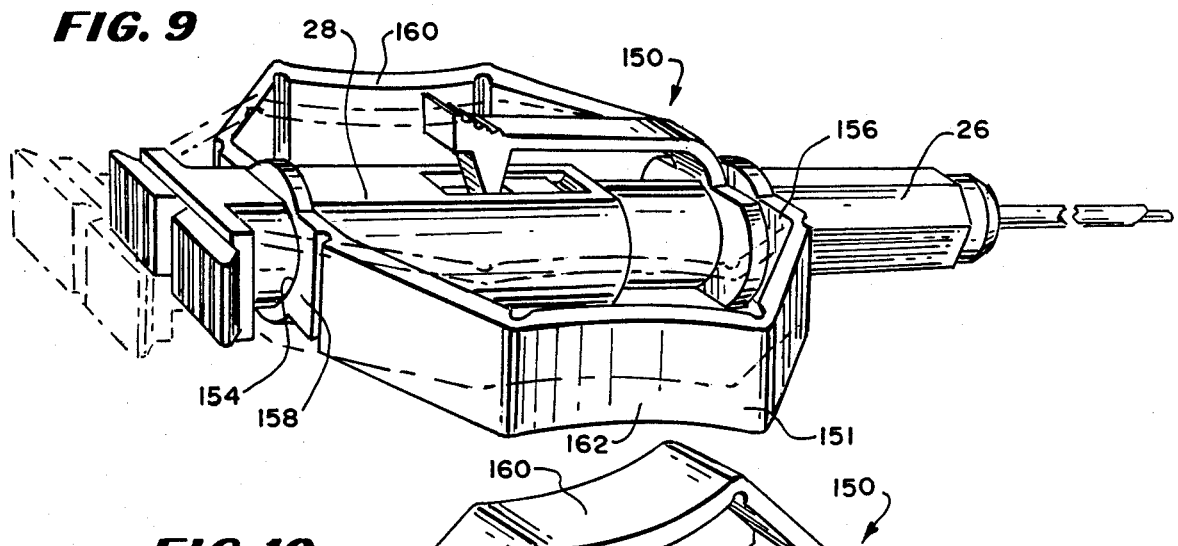
FIG. 9 is a perspective view of yet another embodiment of an octagon shaped arming device of the present invention and shows, in phantom, distortion of the arming device to cause longitudinal separation of a member of a biopsy instrument.
Figure 10:
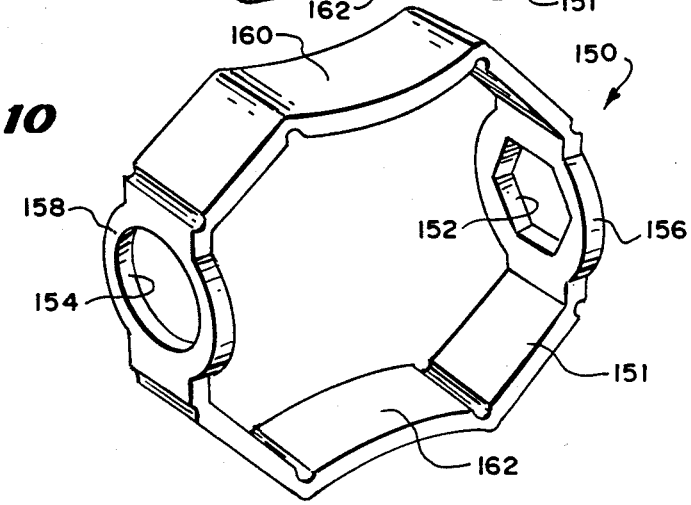
FIG. 10 is a perspective view of the arming device shown in FIG. 9 detached from the biopsy instrument.

Turning now to FIGS. 9 and 10, there is shown therein an alternative embodiment of an arming device 150. Here it will be seen that the ring 14 of the arming device 10 is replaced by a octagon member 151 of the arming device 150 which has openings 152 and 154 in opposite side wall portions 156 and 158 for receiving the barrel members 26 and 28, respectively.

In this device 150, however, the openings 152 and 154 are specifically configured to engage the respective barrels 26 and 28.

As shown in FIG. 10, the opening 152 has a hexagonal configuration to fit over a hexagonal barrel member 26, which has a hexagonal circumference, by being slid over a distal or forward end thereof and snapped or engaged within a groove (not shown) on the barrel member 26.

The opening 154, on the other hand, has a partially circular configuration, identical to the circumferential configuration of the barrel member 28. The wall portion 158 around the opening 154 is slid over a distal or forward end of the barrel member 28 prior to assembly of the two barrel members 26 and 28 together to form the biopsy instrument 20. The device 150 then becomes a part of the biopsy instrument 20 when its assembly is completed.

In use, two side wall portions 160 and 162 of the octagon member 151 are squeezed inwardly, toward the biopsy instrument 20, to obtain a separation of the barrels 26 and 28 in the longitudinal direction, as shown in phantom in FIG. 9. This separation of members 26 and 28, is accomplished with one hand 24 of the user.

The arming devices 10, 60, 110 and 150 of the present invention have a number of advantages, some of which have been described above and others of which are inherent in the invention. For example, manipulation of the biopsy instrument 20 or the syringe 64 using the arming devices 10, 60, 110 or 150 for the taking of a biopsy, may be performed single handedly, which is of importance when working in tight body spaces of a patient, such as within the oral cavity, the rectum, the vagina, etc. and allows the other hand of the user to be freed for external palpation over the biopsy area, for removing the biopsy needle from within the instrument to ensure a good specimen, etc.

Also, modifications may be made to the arming devices of the present invention without departing from the teachings thereof. Accordingly, the invention is only to be limited as necessitated by the accompanying claims.

I claim:

1. An arming device for use in manipulating with one hand a medical instrument comprising first and second telescoping members, said instrument members being longitudinally movable relative to one another along a longitudinal axis, said device comprising:
    an arcuate flexible member having a forward portion and a rearward portion;
    first means at said forward portion for engaging the first telescoping member and second means at said rearward portion for engaging the second telescoping member, said first means for engaging and said second means for engaging being generally coaxial with the longitudinal axis of the instrument, whereby squeezing of said flexible member laterally toward said instrument causes the first and second telescoping members to move longitudinally away from each other thereby to cause arming or operation of the instrument.

2. The arming device of claim 1 wherein said arcuate flexible member is circular.

3. The arming device of claim 1 wherein said arcuate flexible member is hexagonal.

4. The arming device of claim 1 wherein said arcuate flexible member is in the shape of the outer envelope of half of a pear.

5. The arming device of claim 1 combined with a medical instrument comprising a syringe.

6. The arming device of claim 1 combined with a medical instrument comprising a core biopsy instrument.

7. The arming device of claim 1 wherein said first means for engaging includes an edge of a first opening in said arcuate flexible member and said second engaging means includes an edge of a second opening in said arcuate flexible member, said openings being axially aligned, said first opening being adapted to receive and hold one end of said first telescoping member of said instrument therein and the said second opening being adapted to receive the other end of said second telescoping member of said instrument therein.

8. The arming device of claim 7 wherein said arcuate flexible member has a first end wall and a second end wall and said first opening extends laterally from an edge of said arcuate flexible member into said first end wall and said second opening extends through said second end wall.

9. The arming device of claim 7 combined with a core biopsy instrument having a first formed telescoping member, said first forward telescoping member having an annular groove therein adapted to engage said edge of said first opening, a second rearward telescoping member, a rear flange on said second rearward telescoping member, said second telescoping member being slidably received in said second opening and said rear flange of said second telescoping member forming abutment means against which portions of said arcuate flexible member around said second opening abut.

10. The arming device of claim 7 combined with a syringe, said arming device including a sleeve portion adapted to be received about a syringe barrel, said sleeve portion having a collar around a forward end thereof and said collar having a peripheral groove therein which is adapted to mate with one of said openings in said flexible member.

11. The arming device and syringe of claim 10 wherein one of said openings in said flexible member is sized and configured to receive a shaft of a plunger of said syringe therein.

12. The arming device of claim 1 wherein said flexible member comprises an arcuate hemicircular elongate strip of flexible material, said strip having a collar at a proximal end thereof and a sleeve at a distal end thereof.

13. The arming device of claim 12 wherein said collar engages over and onto a shaft of a syringe plunger.

14. The arming device of claim 12 wherein said sleeve engages over and onto a barrel of a syringe.

15. The arming device of claim 1 wherein said device is made of stainless steel.

16. The arming device of claim 1 wherein said device is made of polycarbonate.

17. The arming device of claim 1 wherein said device is made of polypropylene.

18. The arming device of claim 1 wherein said device is made of ABS.

19. A method of using an arming device for use in single handedly operating a medical instrument comprising at least two telescoping members longitudinally moveable relative to one another along a longitudinal axis, and the device comprising an arcuate flexible member having first and second means for engaging opposite ends of the telescoping members of the instrument at forward and rearward ends of the flexible member, said first and second means being generally coaxial with the longitudinal axis, said method comprising the steps of:

connecting a distal end of a distal longitudinally moveable telescoping member of the medical instrument to first engaging means of the device;

connecting a proximal end of a proximal longitudinally movable telescoping member of the medical instrument to second engaging means of the device, said second engaging means being spaced from said first engaging means;

placing an assembly of the device with the instrument members engaged thereto in the palm of the hand; and placing a squeezing force, directed laterally toward the instrument, upon at least an area of the device which lies alongside the medical instrument between the engaging means to flex the device, elongate the device along an axis parallel to the longitudinal axis of the instrument to cause the telescoping members of the instrument to move longitudinally away from one another.

20. The method of claim 19 wherein said steps of connecting include connecting a syringe barrel and a syringe plunger to opposed ends of said flexible member.

21. The method of claim 19 wherein said steps of connecting include connecting a forward barrel member and a rear barrel member of a biopsy instrument to opposed ends of said flexible member.

* * * * *